(12) United States Patent
Ponce et al.

(10) Patent No.: US 11,034,841 B2
(45) Date of Patent: *Jun. 15, 2021

(54) CARBON BLACK IN EFFECT PIGMENTS

(71) Applicants: Lizzabeth Ponce, Lake Jackson, TX (US); Geoffrey Johnson, Wappinger Falls, NY (US); Louis R. Cerce, Garrison, NY (US); Steven Jones, Budd Lake, NJ (US); Curtis Zimmermann, Cold Spring, NY (US)

(72) Inventors: Lizzabeth Ponce, Lake Jackson, TX (US); Geoffrey Johnson, Wappinger Falls, NY (US); Louis R. Cerce, Garrison, NY (US); Steven Jones, Budd Lake, NJ (US); Curtis Zimmermann, Cold Spring, NY (US)

(73) Assignee: BASF Corporation, Florham Park, NJ (US)

( * ) Notice: Subject to any disclaimer, the term of this patent is extended or adjusted under 35 U.S.C. 154(b) by 454 days.

This patent is subject to a terminal disclaimer.

(21) Appl. No.: 14/579,032

(22) Filed: Dec. 22, 2014

(65) Prior Publication Data

US 2016/0145437 A1 May 26, 2016

Related U.S. Application Data

(60) Provisional application No. 62/083,541, filed on Nov. 24, 2014.

(51) Int. Cl.
| | | |
|---|---|---|
| *C09C 1/00* | (2006.01) | |
| *A61Q 19/00* | (2006.01) | |
| *B05D 1/18* | (2006.01) | |
| *A61K 8/02* | (2006.01) | |
| *A61Q 1/06* | (2006.01) | |
| *A61Q 1/10* | (2006.01) | |
| *A61Q 1/08* | (2006.01) | |
| *A61Q 3/02* | (2006.01) | |
| *A61Q 1/12* | (2006.01) | |
| *A61K 8/19* | (2006.01) | |

(52) U.S. Cl.
CPC .......... *C09C 1/0015* (2013.01); *A61K 8/0266* (2013.01); *A61K 8/19* (2013.01); *A61Q 1/06* (2013.01); *A61Q 1/08* (2013.01); *A61Q 1/10* (2013.01); *A61Q 1/12* (2013.01); *A61Q 3/02* (2013.01); *C09C 1/0024* (2013.01); *C09C 1/0045* (2013.01); *C09C 1/0075* (2013.01); *A61K 2800/412* (2013.01); *A61K 2800/436* (2013.01); *C01P 2004/20* (2013.01); *C09C 2200/102* (2013.01); *C09C 2220/10* (2013.01); *C09C 2220/106* (2013.01)

(58) Field of Classification Search
CPC .......... A61K 2800/436; A61K 2800/63; A61K 2800/10; A61K 8/0258; A61K 8/0266; A61K 8/19; A61K 8/25; A61K 8/29; C01P 2004/20; C01P 2004/01; C01P 2006/60; C09C 1/0015; C09C 1/0024; C09C 1/0045

See application file for complete search history.

(56) References Cited

U.S. PATENT DOCUMENTS

| | | | |
|---|---|---|---|
| 4,076,551 A * | 2/1978 | Bernhard | B82Y 30/00 |
| | | | 106/415 |
| 4,084,983 A | 4/1978 | Horst et al. | |
| 4,755,229 A | 7/1988 | Armanini | |
| 5,008,143 A | 4/1991 | Armanini | |
| 5,156,678 A | 10/1992 | Glausch | |
| 6,325,847 B1 | 12/2001 | Christie et al. | |
| 6,440,208 B1 | 8/2002 | Christie et al. | |
| 6,475,273 B1 | 11/2002 | Zimmerman et al. | |
| 6,508,876 B1 * | 1/2003 | Bernhardt | C08K 9/02 |
| | | | 106/415 |
| 6,875,264 B2 | 4/2005 | Zimmermann et al. | |
| 7,517,404 B2 | 4/2009 | Bujard et al. | |
| 8,916,236 B2 | 12/2014 | Bujard | |
| 2008/0168924 A1 * | 7/2008 | Melson | A61K 8/25 |
| | | | 106/426 |

FOREIGN PATENT DOCUMENTS

| | | |
|---|---|---|
| GB | 2 268 504 B | 4/1996 |
| WO | WO-01/29137 A1 | 4/2001 |
| WO | WO-2004/104109 A2 | 12/2004 |
| WO | WO-2016/085874 A1 | 6/2016 |

OTHER PUBLICATIONS

Material Safety Data Sheet for Carbon Black Dispersion, printed Jun. 15, 2005.
Non-Final Office Action in U.S. Appl. No. 14/949,439, dated Mar. 23, 2017 (9 pages).
International Search Report & Written Opinion in International Application No. PCT/US2016/063504, dated Feb. 16, 2017.

* cited by examiner

*Primary Examiner* — Shuangyi Abu Ali
(74) *Attorney, Agent, or Firm* — Foley & Lardner LLP

(57) ABSTRACT

The present application is directed to combination effect pigments comprising an effect pigment and carbon black, wherein the carbon black is adherently deposited on the effect pigment interposed within the substrate and at least one subsequent layer of the effect pigment. This structure of the combination effect pigment results in advantageous non-staining properties of the pigment and maximizes color effects of the carbon black.

23 Claims, No Drawings

CARBON BLACK IN EFFECT PIGMENTS

This application takes the benefit of U.S. provisional application No. 62/083,541 filed Nov. 24, 2014, herein incorporated entirely by reference.

FIELD OF INVENTION

This application is directed to effect pigments containing carbon black and methods of producing these pigments.

BACKGROUND

Effect pigments (sometimes also called gloss pigments, lustrous pigments, pearlescent pigments, interference pigments, or color variable pigments) are well known in the art. A widely used type of effect pigment is mica platelets coated with metallic oxides, such as titanium dioxide. A thin titanium dioxide coating produces a pearl-like or silvery luster. The color produced by this thin layer of $TiO_2$ is a function of optical thickness of the $TiO_2$ layer.

The term "combination pigments" are more complex and may contain a coated platelet such as titanium dioxide (the effect pigment or color variable pigment) coated mica to give a reflected color and an absorption pigment or dye which absorbs some portion of the visible spectrum.

It is these combination pigments that the present application addresses. In particular, this application incorporates carbon black covered by or sandwiched between an additional layer or layers that comprise such color variable pigments. Alternatively, the carbon black can be absorbed onto a porous substrate before the deposition of a layer on the platy substrate. The important requirement to note is the carbon black deposition is followed by an over layer. This over layer or over layers may for example, most typically be a high or low refractive index layer such as a metal oxide or $SiO_2$.

Other low refractive index substances, such as $SiO_2$, may be part of a combination pigment to influence the optical performance. One example is the creation of a color variable pigment as seen in U.S. Pat. No. 6,875,264, herein incorporated entirely by reference, which discloses at least three layer effect pigments having a high refractive index layer, a low refractive index layer followed by a high refractive index layer.

In the past, the coating of carbon black on the surface of effect pigments created a pigment which caused staining. This is especially problematic when such combination pigments are used in cosmetics. The carbon black treated effect pigment leaves a black residue on the skin or clothing.

The objective of the present application is to overlay the carbon black with at least one layer on the platy substrate. This minimizes the amount of free carbon particles on the effect pigment and hence skin/clothing staining. A further objective is to maximize the color effect of the carbon black and the effect pigment.

SUMMARY OF INVENTION

These objectives (non-staining and maximization of color effect) are achieved by the present applicants via the combination effect pigment and the methods described below: A combination effect pigment comprising
  i) an effect pigment, which effect pigment comprises a platelet like substrate and at least one layer, and
  ii) a hydrous oxide or a hydroxide precipitate of carbon black and a polyvalent cation and the carbon black precipitate is between the substrate and the at least one layer and the at least one layer is different than the carbon black precipitate.

The at least one layer may for example be virtually any layer. The at least one layer may be organic or inorganic with the proviso that the at least one layer is different than the carbon black precipitate. Typically the at least one layer is an oxide layer for example a metal oxide or $SiO_2$ layer but may also be a metal layer such as aluminum, silver, brass or bronze.

Further envisioned is a method of preparing the combination effect pigment above.

A method of preparing the combination effect pigment described above comprising
  providing a slurry or suspension of carbon black, platelets and a polyvalent cation,
  forming a hydrous oxide or hydroxide precipitate with the polyvalent cation and carbon black at a given pH,
  forming at least one layer over the precipitate, and
  drying the formed combination effect pigment, with the proviso that the at least one layer is different than the carbon black precipitate.

Additionally, a method of reducing carbon black staining in a combination effect pigment embodied above is envisioned comprising the steps of:
  forming a hydrous oxide or a hydroxide precipitate of carbon black and a polyvalent cation on a platelet substrate and at least partially covering of said precipitate with at least one subsequent layer, with the proviso that the at least subsequent layer is different than the precipitate of carbon black and the polyvalent cation.

DETAILED DESCRIPTION OF THE INVENTION

Effect Pigment

Effect pigments are well known in the art and comprise a flake or platelet substrate which is coated with a reflecting layer. The reflection color is a function of optical thickness of the layer or layers on the substrate.

Combination Effect Pigment

The term "combination effect pigment" means a combination of two types of color producing phenomena within the same pigment. In particular the combination effect pigment produces color as a function of optical thickness of a layered coating (i.e. $TiO_2$ coatings on mica) on a substrate, that is a reflecting layer which is a function of optical thickness and deposition of an absorbing colorant on the same substrate as in the present case, carbon black.

Optical Layer

This term is well known in the art and refers to a coating or layer on a substrate where the coating or layer reflects color and the color is a function of the optical thickness of the coating, that is the geometrical thickness times the refractive index of the coating. An optical thickness of about 80 nm to about 140 nm produce reflections which may be called white, silvery or pearly and optical thicknesses of about 190 nm or more produce colored reflections. Typically the optical coating or layer will range from about 60 nm to about 800 nm. The optical layer is most typically a metal oxide layer.

At Least One Layer

The phrase "at least one layer" for purposes of this application means any layer at all. The layer may be organic or inorganic. The "at least one layer" may be of high refractive index, that is greater than or equal to 1.65 or of low refractive index, that is of less than 1.65. The "at least one layer" may be a metal oxide selected from the group of metal oxides consisting of $TiO_2$, $In_2O_3$, $ZrO_2$, $Fe_2O_3$, $Fe_3O_4$, $Cr_2O_3$, $CeO_2$, ZnO, $SnO_2$ and mixtures thereof. The metal oxides $TiO_2$, $Cr_2O_3$, $Fe_2O_3$ and $SnO_2$ are most typical. Furthermore, the "at least one layer" may be a metal oxide, $SiO_2$, a metal such brass, bronze, silver or aluminum.

There may be multiple layers on the substrate over layering the carbon black deposition and these may be formed from the as above metal oxide, $SiO_2$, a metal such as brass, bronze, silver and aluminum.

Substrate

The term "substrate" for purposes of this disclosure means platy inorganic or organic treated or untreated materials. For example, such platy materials may include aluminum oxide, platy glass, perlite, aluminum, natural mica, synthetic mica, bismuth oxychloride, platy iron oxide, platy graphite, platy silica, bronze, stainless steel, natural pearl, boron nitride, copper flake, copper alloy flake, zinc flake, zinc alloy flake, zinc oxide, enamel, china clay, porcelain, titanium oxide, platy titanium dioxide, titanium suboxide, kaolin, zeolites and combinations thereof.

Thus the substrate is selected from the group consisting of iron oxide, synthetic mica, natural mica, basic lead carbonate, flaky barium sulfate, $SiO_2$, $Al_2O_3$, $TiO_2$, glass flakes, ZnO, $ZrO_2$, $SnO_2$, BiOCl, chromium oxide, BN, MgO flakes, $Si_3N_4$, graphite, aluminum, titanium, aluminum alloys, bronzes, iron and perlite, most typically the platelets are selected from the group consisting of synthetic mica, natural mica, $SiO_2$ flakes, $Al_2O_3$ flakes, $TiO_2$ flakes, $Fe_2O_3$ flakes, BiOCl and glass flakes.

As defined above the substrate may be treated or untreated. For example, the substrate may be treated with virtually any agent such silicones and coupling agents. Alternatively, the substrate may be mechanically treated to smooth the surface, or plasma or radiation treatments to activate the surface before application of the at least one layer, or the carbon black precipitate.

The platelet like substrate may also be a mixture of identical or different substrates, each having different particle sizes. The substrate mixture can consist of two, three or more different substrates. Preference is given to one substrate, say for example natural mica, synthetic mica or glass flakes.

There may be some advantage of using porous substrates when applying the carbon black to the substrate directly or onto a $SiO_2$ layer. The porous substrate or silica coated substrate can be treated with carbon black via incipient wetness impregnation. Incipient wetness is a process in which a solid support is impregnated with the maximum amount of solution that it can absorb without having any excess solution. After impregnation, the material is dried. In the present case the solution is the carbon black dispersion containing the polyvalent cation.

Platy, Platelet or Platelet Like

The descriptor "platy" as used herein is well understood in the art. The term "platy" may be used interchangeably with flake, flake-like, plate-like, platelet and flaky.

The platelet has two dimensions (length and width) of similar magnitude and characteristically much greater than the third dimension, the thickness of the platelet. The platelets are useful as substrates for the application of the metal oxide coating and/or $SiO_2$ and deposition of the carbon black via hydrous oxide or hydroxide precipitate of the polyvalent cation.

The substrate may be further characterized in a number of ways. For example, the platelet substrate diameter may range from about 0.1 to about 350 microns, preferably about 5 to about 250 microns and most preferably from about 1 to about 150 microns. Most typically the platelet ranges from about 5 to about 50 or about 100 microns.

Carbon Black

The carbon black of interest can be virtually any carbon black but of special interest is the cosmetically approved Carbon Black No. 2.

The carbon black is deposited onto the substrate via hydrous oxide or hydroxide precipitate with a polyvalent cation at a given pH.

The carbon black may first be dispersed in an aqueous medium in the presence of nonionic surfactants and/or anionic polymers before addition to the platelet slurry. Without the dispersion of the carbon black, the carbon black would have a tendency to agglomerate and not deposit on the substrate when the hydrous or hydroxide precipitate is formed. Thus for example, the carbon black is most typically in a dispersed form when combined with the platelet before precipitation with the polyvalent cation onto the platelets or substrate.

The combination effect pigment will typically have a carbon black loading on the substrate ranging from about 0.01 to about 3 wt. %, for example about 0.1 to about 0.8 wt. %, or about 0.1 to about 0.5 wt. % based on the total weight of the uncoated substrate.

The Polyvalent Cation

The polyvalent cation exists as a salt in an aqueous medium at the appropriate pH with a suitable anionic counterion for example selected from the group consisting of chloride, nitrate and sulfate.

Any polyvalent cation which will form a precipitate under the given pH conditions can be used.

The polyvalent cation is typically selected from the group consisting of Al, Cr, Ti, Zn, Mg, Zr, Fe and Sn, most typically Al and Cr. More specifically the polyvalent cation is selected from the group consisting of Al(III), Cr(III), Zn(II), Mg(II), Ti(IV), Zr(IV), Fe(II), Fe(III) and Sn(IV).

There are particular advantages using Cr(III). When using $CrCl_3 \cdot 6H_2O$ the precipitate formed with Cr(III) shows no agglomeration issues.

The formation of the hydrous or hydroxide precipitate works to deposit on the substrate platelets a complex of a metal hydroxide or hydrous oxide which carries the carbon black dispersed particles with it, to produce the combination effect pigment with an adherent film on the platelets. This adherent film is sealed or overlayed with "the at least one layer".

The weight percent of polyvalent cation ranges from about 0.01 to about 1 wt. %, for example about 0.05 to about 0.9 wt %, about 0.1 to about 0.5 wt. % based on the total weight of the uncoated substrate.

Furthermore the weight ratio of carbon black to the polyvalent cation ranges from about 3 to 1 to about 1 to 3, for example about 2 to about 1 to about 1 to 2, typically about 1 to about 1.5 to about 1.5 to about 1.

For example the carbon black may deposit on the substrate giving a wt. ranging from 0.1 to 0.5 and the polyvalent cation weight percent may range from about 0.1 to about 0.5 wherein the wt. % is based on the total weight of the uncoated substrate. This would give a wt. ratio of carbon black to polyvalent cation ranging from about 0.2 to about 5 to 5 to about 0.2, more typical ratios are for example about 0.5 to about 3 to about 3 to about 0.5.

The Carbon Black Precipitate

For purposes of this application when the phrase "carbon black precipitate" is used, what is meant is the hydrous oxide or hydroxide precipitate formed in the presence of carbon black and a polyvalent cation at a given pH. The pH range for the deposition depends on the particular polyvalent cation being employed. For example Al and Cr(III) will form an hydrous oxide or hydroxide precipitate between 4 and 9.

The hydrous oxide or hydroxide precipitate functions as a kind of glue which helps the carbon black to deposit directly onto the substrate.

The carbon black precipitate is deposited either directly onto a substrate or onto one of the layers on the substrate. However the carbon black precipitate will always be interposed between the substrate and the "at least one layer". The covering layer covers substantially the carbon precipitate layer. The covering layer may be as explained above typically a metal oxide, $SiO_2$ or a metal such as brass, bronze, silver or aluminum.

Important embodiments include:

A combination effect pigment comprising
 i) an effect pigment, which effect pigment comprises a platelet like substrate and at least one layer, and
 ii) a hydrous oxide or a hydroxide precipitate of carbon black and a polyvalent cation and the carbon black precipitate is between the substrate and the at least one layer, with the proviso that the at least one layer and the precipitate of carbon black are different.

Further specific embodiments include:

The combination effect pigment wherein the at least one layer is an optical layer.

The combination effect pigment wherein the at least one layer is a $SiO_2$ layer.

The combination effect pigment wherein the precipitate is between the substrate and the at least one layer.

The combination effect pigment wherein the combination effect pigment comprises only one optical layer.

The combination effect pigment wherein the precipitate is interposed between two optical layers.

The combination effect pigment wherein the precipitate is interposed between an optical layer and an $SiO_2$ layer The combination effect pigment wherein the precipitate is in direct contact with the substrate.

To illustrate, the layered structure of the combination effect pigment may be any of the structures below:

Substrate/Carbon Black Precipitate/$SiO_2$
Substrate/Carbon Black Precipitate/$TiO_2$
Substrate/$TiO_2$/Carbon Black Precipitate/$TiO_2$
Substrate/Carbon Black Precipitate/$TiO_2$/$SiO_2$
Substrate/$TiO_2$/Carbon Black Precipitate/$SiO_2$
Substrate/$SiO_2$/$TiO_2$/Carbon Black Precipitate/$Fe_2O_3$
Substrate/$TiO_2$/Carbon Black/$SiO_2$/Carbon Black Precipitate/$TiO_2$
Substrate/$Fe_2O_3$/$SiO_2$/Carbon Black Precipitate/$TiO_2$/$SiO_2$
Substrate/$SnO_2$/$TiO_2$/Carbon Black Precipitate/$TiO_2$
Substrate/$TiO_2$/$SiO_2$/Carbon Black Precipitate/$Fe_2O_3$
Substrate/$TiO_2$/$SiO_2$/Carbon Black Precipitate/$TiO_2$
Substrate/$TiO_2$/Carbon Black Precipitate/$SiO_2$/$Fe_2O_3$
Substrate/$TiO_2$/Carbon Black Precipitate/$SiO_2$/$TiO_2$
Substrate/$Fe_2O_3$/$SiO_2$/Carbon Black Precipitate/$Fe_2O_3$
Substrate/$Fe_2O_3$/$SiO_2$/Carbon Black Precipitate/$TiO_2$
Substrate/$Fe_2O_3$/Carbon Black Precipitate/$SiO_2$/$Fe_2O_3$
Substrate/$Fe_2O_3$/Carbon Black Precipitate/$SiO_2$/$TiO_2$
Substrate/$TiO_2$/$SiO_2$/Carbon Black Precipitate/$Cr_2O_3$ Method of Preparing the Combination Effect Pigment The method of preparing anyone of the embodiments of the combination effect pigment described above comprises the steps:
 providing a slurry or suspension of carbon black, platelets and a polyvalent cation,
 forming a hydrous oxide or hydroxide precipitate with the polyvalent cation and carbon black at a given pH,
 forming at least one layer over the precipitate on the platelets, and
 drying the formed combination effect pigment, with the proviso that the at least one layer is different than the carbon black precipitate.

The suspension of platelets and the carbon black is best if the platelets and carbon black are well dispersed. The pH of the platelets with carbon black and polyvalent cation (usually a salt form) is typically acidic as this gives a well dispersed water soluble salt of the polyvalent cation. The pH of the resulting suspension is then adjusted to form a precipitate of the desired polyvalent cation hydroxide or hydrous oxide, generally between about 1 to 10. The pH should be sufficient to precipitate the hydrous oxide or hydroxide of the polyvalent cation.

The carbon black is deposited along with the hydroxide or hydrous oxide cation on the platelets to form a smooth, uniform coating. The suspension can then be further treated to form at least one layer over the formed precipitate on the platelets.

The platelets themselves in the suspension or slurry (before deposition of the carbon black) can be previously treated with for example metal oxide layers or $SiO_2$ layers. Further the at least one layer may be present in various crystalline forms, for example, $TiO_2$ can be anatase or rutile.

Any polyvalent cation which will form a precipitate under given pH conditions can be used. Such polyvalent cations are employed in the form of a solution of a soluble salt. Thus, the cation can be for example, one or more of Al(III), Cr(III), Zn(II), Mg(II), Ti(IV), Zr(IV), Fe(II), Fe(III), Ce(III) and Sn(IV). Suitable anions include chloride, nitrate, sulfate and the like.

The pH range for deposition depends on the particular cation being employed. The formation of the hydroxide or hydrous precipitate is typically carried out by the addition of a soluble base, such as sodium hydroxide, potassium hydroxide or ammonia solution where the desired pH of the precipitation is higher than the pH of the salt solution.

Further the application is directed to a method of reducing carbon black staining in an effect pigment according to anyone of the combination effect pigment embodiments described above comprising the steps of:
 forming a hydrous oxide or a hydroxide precipitate of carbon black and a polyvalent cation on a platelet substrate and at least partially covering of said precipitate with at least one subsequent layer, with the proviso that the at least one subsequent layer is different than the precipitate of carbon black and the polyvalent cation.

The Applicants have found that the deposition followed by application of a covering layer over the deposited carbon black minimizes the amount of free carbon particles and hence skin staining.

Applications of the Inventive Combination Effect Pigment

The effect pigments according to the invention can be used for all customary purposes, for example for coloring polymers in the mass, coatings (including effect finishes, including those for the automotive sector) and printing inks (including offset printing, intaglio printing, gravure, bronzing and flexographic printing), and also for applications in cosmetics, in ink-jet-printing, for dyeing textiles, as well as laser marking of papers and plastics. Such applications are known from reference works, for example "Industrielle Organische Pigmente" (W. Herbst and K. Hunger, VCH Verlagsgesellschaft mbH, Weinheim/New York, 2$^{nd}$, completely revised edition, 1995).

A paint, coating, printing ink, plastic, cosmetic formulation, laser marking, pigment composition or dry preparation, especially a cosmetic formulation comprising the inventive combination effect pigment are important embodiments of the present disclosure.

In one embodiment, the composition is part of a cosmetic composition. The form of the cosmetic composition can be any form normally used for cosmetics such as cream, emulsion, foam, gel, lotion, milk, mousse, ointment, paste, powder, spray, or suspension. The cosmetic composition can be any colored cosmetic used on the skin, hair, eyes, or lips, such as concealing sticks, foundation, stage make-up, mascara (cake or cream), eye shadow (liquid, pomade, powder, stick, pressed or cream), hair color, lipsticks, lip gloss, kohl pencils, eye liners, blushers, eyebrow pencils, and cream powders. Other exemplary cosmetic compositions include, but are not limited to, nail enamel, skin glosser stick, hair sprays, face powder, leg-makeup, insect repellent lotion, nail enamel remover, perfume lotion, and shampoos of all types (gel or liquid). In addition, the claimed compositions can be used in shaving cream (concentrate for aerosol, brushless, lathering), hair groom, cologne stick, cologne, cologne emollient, bubble bath, body lotion (moisturizing, cleansing, analgesic, astringent), after shave lotion, after bath milk and sunscreen lotion. For a review of cosmetic applications, see Cosmetics: Science and Technology, 2nd Ed., Eds: M. S. Balsam and Edward Sagarin, Wiley-Interscience (1972) and deNavarre, The Chemistry and Science of Cosmetics, 2nd Ed., Vols 1 and 2 (1962), Van Nostrand Co. Inc., Vols 3 and 4 (1975), Continental Press, both of which are hereby incorporated by reference.

The cosmetic composition optionally comprises at least one cosmetically acceptable auxiliary agent. Cosmetically acceptable auxiliary agents include, but are not limited to, carriers, excipients, emulsifiers, surfactants, preservatives, fragrances, perfume oils, thickeners, polymers, gel formers, dyes, absorption pigments, photo protective agents, consistency regulators, antioxidants, antifoams, antistats, resins, solvents, solubility promoters, neutralizing agents, stabilizers, sterilizing agents, propellants, drying agents, opacifiers, cosmetically active ingredients, hair polymers, hair and skin conditioners, graft polymers, water-soluble or dispersible silicone-containing polymers, bleaches, care agents, colorants, tinting agents, tanning agents, humectants, refatting agents, collagen, protein hydrolyzates, lipids, emollients and softeners, tinting agents, tanning agents, bleaches, keratin-hardening substances, antimicrobial active ingredients, photofilter active ingredients, repellant active ingredients, hyperemic substances, keratolytic and keratoplastic substances, antidandruff active ingredients, antiphlogistics, keratinizing substances, active ingredients which act as antioxidants and/or as free-radical scavengers, skin moisturizing or humectants substances, refatting active ingredients, deodorizing active ingredients, sebostatic active ingredients, plant extracts, antierythematous or antiallergic active ingredients and mixtures thereof. Cosmetic formulations are known in the art. See, for instance, US Publication Nos. 20080196847 and 20100322981.

The inventive combination effect pigment may be added in any tinctorially effective amount to the paint, coating, printing ink, high molecular weight organic material, cosmetic formulation, laser marking, pigment composition or dry preparation.

The inventive combination effect pigment may be added to such materials as paint, coating, printing ink, high molecular weight organic material, cosmetic formulation, laser marking, pigment composition or dry preparation at concentrations ranging for 0.0001 to about 90 wt. %, for example about 0.001 to about 80 wt. %, especially 0.01 to about 50 wt. % wherein the wt. % is based on the total weight of the material.

In regard to cosmetic formulations the inventive combination effect pigment may be added from about 0.0001 to 90 wt. % based on the total weight of the cosmetic formulation. The cosmetic formulation most likely will further contains a cosmetically suitable carrier material ranging from about 10 to about 90 wt. %. The cosmetically suitable carrier material is preferably different than water.

Accordingly a paint, ink-jet, coatings, printing ink, plastic, cosmetic, glazes for ceramics and glass may contain the combination effect pigment as described in the summary of the invention above.

Furthermore, the application of particular interest is a cosmetic containing the combination effect pigment as described in the summary of the invention above.

The cosmetic comprising the combination effect pigment may be for example, in the form of sticks, ointments, creams, emulsions, suspensions, dispersions, powders or solutions.

Particular cosmetics comprising the inventive combination effect pigment is for example a lipstick, mascara preparation, blusher, eye-shadows, foundation, eyeliners, powder or nail varnishes.

EXAMPLES

Example 1

Carbon Black on Titania Coated Mica

A 13% aqeous slurry containing 100 grams of titania coated mica with gold interference color was heated to 78° C. and stirred. The pH was adjusted to 3.0 using 20% w/w aq. HCl followed by the dumping of a carbon black dispersion (20% Solids) for a 3.0 wt % coating. The slurry was treated with 4.3% w/w aq. Al(NO$_3$)$_3$ for a 0.8 wt % treatment. The slurry was then stirred for at least 10 minutes. Precipitation was further promoted by pumping of 3.5% w/w aq. NaOH at 1.5 mL/min and raising the pH to 8.0. The slurry was then allowed to stir for at least 30 minutes. Following the reaction described, the slurry was filtered, washed and dried at 120° C. The carbon black treated titania coated mica was compared to the untreated titania coated mica, as a drawdown comprised of 3% pigment in lacquer. The gold shade in the treated titanium coated mica was darkened. The bulk color of the treated titanium oxide coated mica was visibly gold, unlike the white bulk color observed for the untreated titanium oxide coated mica.

Example 2

Carbon on Titania Coated Borosilicate Flake

A 33% aqueous slurry containing 200 g of titanium oxide coated borosilicate flakes with a pearl interference color was heated to 78° C. and stirred. The pH was adjusted to 3.0 using 20% w/w aq. HCl. At pH 3.0, 20% w/w aq. carbon black dispersion is dumped for a 1.5 wt % coating. The slurry was treated with 4.3% w/w aq. Al(NO$_3$)$_3$ for a 0.8 wt % treatment followed by at least a 10 minutes stir. Precipitation was further promoted by pumping of 3.5% w/w aq. NaOH at 1.5 mL/min and raising the pH to 8.0. The slurry was then allowed to stir for at least 30 minutes. Following the reaction described, the slurry was filtered, washed, and dried at 120° C. The treated product was compared to untreated titania coated borosilicate, as a drawdown comprised of 12% pigment in a lacquer. An enhanced darkened pearl shade was observed in the treated product compared to untreated starting titanium oxide coated borosilicate flakes. Further, the bulk color of the carbon treated flakes was clearly a silver pearl compared to the white bulk color observed in the untreated flakes.

Example 3

Carbon Black in an Effect Pigment—Carbon on the 1$^{st}$ TiO$_2$ Layer Using Al(NO$_3$)$_3$ A 33% aqueous slurry containing 832 g of glass flakes (5 micron thickness and 100 microns mean diameter) was heated to 80° C. and stirred. The pH was adjusted to 1.35 with 28% aq. w/w HCl, then 47 g of 20% w/w SnCl$_4$ solution were pumped in at a pH of 1.35 at 1.94 mL/min. A 40% w/w aq. TiCl$_4$ solution was then pumped at 1.5 ml/min to match a pearl shade. The pH was adjusted to 3.0 for the addition of Carbon Black. The 20% Carbon Black dispersion was dumped in for a 0.2 wt % coating. The Carbon dump is followed by the addition of 4.3% w/w aq. Al(NO$_3$)$_3$ for a 0.1 wt % treatment. Precipitation was further promoted by pumping 3.5% w/w NaOH and raising the pH to 8.0 at 1.5 mL/min. The slurry was then allowed to stir for at least 30 minutes. At pH 8.0, 458.7 g of 20% w/w aq. Na$_2$SiO$_3$.5H$_2$O aqueous solution are pumped at 4.0 g/min using 28% w/w HCl to control the pH. Following the Na$_2$SiO$_3$.5H$_2$O addition, pH is adjusted to 1.4 by pumping 28% w/w HCl at 2.9 g/min for SnCl$_4$ addition. Then 47 g of 20% w/w SnCl$_4$ solution was added at 2.4 g/min using 35% w/w aq. NaOH to control the pH, followed by 164 g of 40% w/w TiCl$_4$ using 35% w/w NaOH to control the pH at 1.4. Following the reaction described, the slurry was filtered, washed, and heat-treated at 400° C. The carbon black treated flakes were compared to flakes made without the carbon black treatment, as a drawdown comprised of 12% pigment in SLF2 lacquer. A much darker pearl shade was observed in the treated flakes compared to flakes prepared without the carbon black treatment. The bulk color of the inventive flakes was a dark pearl in contrast to the colorless bulk of the flakes not treated with carbon black.

Note: Using this same procedure carbon can be incorporated on any of the layers that comprise the effect pigment described.

Example 4

Carbon Black in an Effect Pigment—Carbon on the 1$^{st}$ TiO$_2$ Layer Using CrCl$_3$.5H$_2$O A 33% aqueous slurry containing 832 g of glass flakes (5 micron thickness and 100 microns mean diameter) was heated to 80° C. and stirred. The pH was adjusted to 1.35 with 28% w/w aq. HCl, then 47 g of a 20% w/w aq. SnCl$_4$ solution were pumped in at a pH of 1.35 at 1.94 mL/min. A 40% w/w aq. TiCl$_4$ solution was pumped at 2.4 g/min to match a pearl shade. The pH was raised to 3.0 for the addition of Carbon Black. The 20% Carbon Black dispersion was dumped in for a 0.3 wt % coating. The pH was raised to 6.8 using 3.5% w/w aq. NaOH, then 1.5% w/w aq. CrCl$_3$.5H$_2$O was pumped in for a 0.5 wt % treatment using 3.5% w/w NaOH to maintain pH. Precipitation was further promoted by pumping of 3.5% w/w NaOH and raising the pH to 7.5. The slurry was then allowed to stir for at least 20 minutes. At pH 8.0, 458.7 g of 20% w/w aq. Na$_2$SiO$_3$.5H$_2$O aqueous solution was pumped at 4.0 g/min using 28% w/w aq. HCl to control the pH. Following the Na$_2$SiO$_3$.5H$_2$O addition, pH was adjusted to 1.4 for SnCl$_4$ addition by pumping 28% w/w HCl at 2.9 g/min, followed by 47 g of 20% w/w SnCl$_4$ solution added at 1.94 mL/min using 35% w/w NaOH to control the pH. Next, 164 g of 40% w/w TiCl$_4$ were then pumped at 2.4 g/min using 35% w/w NaOH to control the pH. Following the reaction described, the slurry was filtered, washed, and heat-treated at 400° C. The carbon treated flakes were compared to the same flakes made above but without carbon black treatment, as a drawdown comprised of 12% pigment in SLF2 lacquer. A much darker pearl shade can be observed for inventive pigment while keeping the sparkle effect observed in untreated flakes. The bulk color of the inventive pigment is also representative of the color observed in the drawdown as opposed to the white bulk color observed for a same pigment without the carbon black treatment.

Note: Using this same procedure carbon can be incorporated on any of the layers that comprise the effect pigment described.

Example 5

Carbon Black in a Violet Effect Pigment; Carbon in the 2nd TiO$_2$ Layer Using CrCl$_3$.5H$_2$O A 13.4% aqueous slurry containing 258 g of glass flakes (1 micron thickness and 80 microns mean diameter) was heated to 82° C. and stirred. The pH is adjusted to 1.3 with 1:1 v/v HCl solution, then 42 g of a 20% w/w aq. SnCl$_4$ solution were pumped in at a pH of 1.3 at 2.2 g/min. A 40% w/w aq. TiCl$_4$ solution was pumped at 2.4 g/min to match a pearl shade. The pH was then increased to 7.8, then 1200 g of 20% aq. w/w Na$_2$SiO$_3$.5H$_2$O was pumped at 4.0 g/min using 28% w/w HCl to control the pH. Following the Na$_2$SiO$_3$.5H$_2$O addition, pH was adjusted to 1.7 then 8.0 g of 20% w/w SnCl$_4$ solution were dumped into the slurry. Next, 90 g of 40% w/w TiCl$_4$ were pumped using 35% w/w NaOH to control the pH. After, the pH was raised to 3.0 for the addition of Carbon Black. The 20% Carbon Black dispersion was dumped into the slurry for a 0.4 wt % coating. The pH was then raised to 6.8 using 3.5% w/w NaOH followed by 1.5% w/w aq. CrCl$_3$.5H$_2$O that was pumped in for a 0.6 wt % treatment using 3.5% w/w NaOH to maintain pH. Precipitation was further promoted by pumping of 3.5% w/w NaOH and raising the pH to 7.5. After a 20 minutes stir, the pH of the slurry was lowered to 1.35. An additional 30 g of 40% w/w TiCl$_4$ were added. Following the reaction described, the slurry was filtered, washed, and heat-treated at 400° C. The treated flakes were compared to the effect pigment prepared in the same way except not treated with carbon black, as a drawdown comprised of 6% pigment in DL101 lacquer. The color travel observed in the inventive pigment was in line with that observed in the untreated violet, red to violet. The bulk color of the treated pigment is of a violet shade.

Note: Using this same procedure carbon can be incorporated on any of the layers that comprise the effect pigment described.

Example 6

Carbon Black in the 2nd TiO$_2$ Layer Using FeCl$_3$

A 13.4% aqueous slurry containing 258 g of glass flakes (1 micron thickness and 80 micron mean diameter) was heated to 82° C. and stirred. The pH was adjusted to 1.3 with 1:1 v/v HCl solution, then 42 g of a 20% w/w aq. $SnCl_4$ solution were pumped in at a pH of 1.3 at 2.2 g/min. Next, a 40% w/w aq. $TiCl_4$ solution is pumped to match a pearl shade. The pH was then increased to 7.8 and 1200 g of 20% w/w $Na_2SiO_3.5H_2O$ aqueous solution was pumped at 4.0 g/min using 28% w/w aq. HCl to control the pH. Following the $Na_2SiO_3.5H_2O$ addition, the pH was adjusted to 1.7 for $SnCl_4$ addition by pumping 28% w/w HCl at 2.9 g/min. After 8.0 g of 20% w/w $SnCl_4$ solution were dumped into the slurry, 97.5 g of 40% w/w $TiCl_4$ were then pumped using 35% w/w NaOH to control the pH. The pH was then raised to 3.0 for the addition of Carbon Black. The 20% Carbon Black dispersion was dumped into the slurry for a 0.4 wt % coating. Next, 2.29% w/w aq. $FeCl_3$ was pumped in for a 0.6 wt % treatment using 3.5% w/w NaOH to maintain pH. The pH was then lowered to 1.35, and an additional 32.5 g of 40% w/w $TiCl_4$ are added. Following the reaction described, the slurry was filtered, washed, and heat-treated at 400° C. The carbon black treated flakes were compared to the same flakes but not coated with carbon black, as a drawdown comprised of 6% pigment in DL101 lacquer. The color travel observed in inventive pigment was in line with that observed in same flakes not treated with carbon black, blue to violet. The bulk color of the inventive flakes was violet.

Example 7

Carbon Black in an Effect Pigment, Carbon in Silica Layer

A 33% aqueous slurry containing 832 g of glass flakes (5 micron thickness and 100 microns mean diameter) was heated to 80° C. and stirred. The pH was adjusted to 1.35 with 1:1 v/v HCl solution, then 47 g of a 20% w/w aq. $SnCl_4$ solution were pumped in at a pH of 1.3 at 2.2 g/min. Next, a 40% w/w aq. $TiCl_4$ solution was pumped at 2.4 g/min to match a pearl shade. The pH was then increased to 7.8, and 1075 g of 20% w/w $Na_2SiO_3.5H_2O$ aqueous solution was pumped at 4.0 g/min using 28% w/w aq. HCl to control the pH. The slurry was filtered, washed, and dried at 120° C. to make the silica intermediate. Then 350 g of the silica intermediate were impregnated with 35 g of 2% w/w aq. Carbon Black dispersion solution via incipient wetness impregnation. The substrate was dried at 120° C. followed by the impregnation of 35 g of 1.5% w/w aq. $Cr(NO_3)_3.9H_2O$ solution. The substrate was dried at 120° C. At this point the bulk color of the pigment was a dark intense gold. Thereafter, the substrate was reslurried in 700 mL water and heated to 82° C. and stirred. The pH was adjusted to 1.6, then 2.7 g of 20% w/w $SnCl_4$ was dumped into the slurry, followed by at least 22 minutes stir. The pH was then adjusted to 1.35 for $TiCl_4$ addition by pumping 28% w/w HCl. Next, 67.6 g of 40% w/w $TiCl_4$ were pumped at 2.4 g/min to match Reflect MultiDimensions® transforming teal. Following the reaction described, the slurry was filtered, washed, and heat-treated at 400° C. A weak color travel from light red to a slight green shade was observed in the bulk color. A similar effect was observed in a drawdown comprised of 6% pigment in DL101 lacquer.

Example 8

Carbon Black in the 2nd $TiO_2$ Layer Using $CrCl_3.5H_2O$

A 13.4% aqueous slurry containing 258 g of glass flakes (1 micron thickness and 80 microns mean diameter) was heated to 82° C. and stirred. The pH was adjusted to 1.3 with 1:1 v/v HCl solution, then 42 g of a 20% w/w aq. $SnCl_4$ solution were pumped in at a pH of 1.3 at 2.2 g/min. A 40% w/w aq. $TiCl_4$ solution was pumped at 2.4 g/min to match a pearl shade. The pH was then increased to 7.8, and 1075 g of 20% aq. w/w $Na_2SiO_3.5H_2O$ were pumped at 4.0 g/min using 28% w/w HCl to control the pH. Following the $Na_2SiO_3.5H_2O$ addition, pH was adjusted to 1.7 for $SnCl_4$ addition. After 8.0 g of 20% w/w $SnCl_4$ addition were dumped into the slurry, 90 g of 40% w/w $TiCl_4$ were then pumped using 35% w/w NaOH to control the pH. The pH was then raised to 3.0 for the addition of carbon black. The 20% Carbon Black dispersion was dumped into the slurry for a 0.4 wt % coating. The pH was raised to 6.8 using 3.5% w/w NaOH, followed by 1.5% w/w aq. $CrCl_3.5H_2O$ that was pumped in for a 0.6 wt % treatment using 3.5% w/w NaOH to maintain pH. Precipitation was further promoted by pumping of 3.5% w/w NaOH and raising the pH to 7.5. After a 20 minutes stir, the pH of the slurry was lowered to 1.35. An additional 50 g of 40% w/w $TiCl_4$ were then added. Following the reaction described, the slurry was filtered, washed, and heat-treated at 400° C. Inventive pigment was compared to pigment without the carbon black treatment, as a drawdown comprised of 6% pigment in DL101 lacquer. The color travel observed in inventive pigment was in line with that observed in the same pigment without the carbon black treatment, red to violet. The bulk color of untreated pigment is of a violet shade.

Note: The use of $CrCl_3.5H_2O$ as the polyvalent cation showed noticeable improvements over $Al(NO_3)_3$. No agglomeration issues were encountered with the use of $CrCl_3.5H_2O$, characteristic of high loadings of $Al(NO_3)_3$.

Cosmetic Applications:

Preliminary tests show that incorporating carbon black into an effect pigment with an over layer is advantageous versus a physical blend of the carbon black and an effect pigment. Skin staining is significantly diminished. Further, incorporating the carbon within a layer is expected to improve upon the external carbon attachment to an effect material.

The invention claimed is:

1. A combination effect pigment comprising
   i) an effect pigment, which effect pigment comprises a platelet like substrate and at least one optical layer, and
   ii) a layer of a hydrous oxide or a hydroxide precipitate of carbon black and a polyvalent cation and the layer of the hydrous oxide or a hydroxide precipitate of carbon black precipitate is between the substrate and the at least one optical layer, and the at least one optical layer is different than the layer of hydrous oxide or hydroxide precipitate of carbon black;
   wherein the weight ratio of hydrous oxide or a hydroxide precipitate of carbon black to the polyvalent cation is from about 3 to 1 to about 1 to 3.

2. The combination effect pigment according to claim 1, wherein the at least one optical layer is a $SiO_2$ layer.

3. The combination effect pigment according to claim 1, wherein the combination effect pigment has only one optical layer.

4. The combination effect pigment according to claim 1, wherein the hydrous oxide or the hydroxide precipitate of carbon black is interposed between two optical layers.

5. The combination effect pigment according to claim 1, wherein the hydrous oxide or the hydroxide precipitate of carbon black is interposed between an optical layer and an $SiO_2$ layer.

6. The combination effect pigment according to claim 1, wherein the hydrous oxide or the hydroxide precipitate of carbon black is in direct contact with the substrate.

7. The combination effect pigment according to claim 1, wherein the optical layer is a metal oxide.

8. The combination effect pigment according to claim 7, wherein the metal oxide is selected from the group consisting of $TiO_2$, $In_2O_3$, $ZrO_2$, $Fe_2O_3$, $Fe_3O_4$, $Cr_2O_3$, $CeO_2$, $ZnO$, $SnO_2$ and mixtures thereof.

9. The combination effect pigment according to claim 1, wherein the substrate is selected from the group consisting of iron oxide, synthetic mica, natural mica, basic lead carbonate, flaky barium sulfate, $SiO_2$, $Al_2O_3$, $TiO_2$, glass, $ZnO$, $ZrO_2$, $SnO_2$, $BiOCl$, chromium oxide, BN, MgO flakes, $Si_3N_4$, graphite, aluminum, titanium, aluminum alloys, bronzes, iron and perlite.

10. The combination effect pigment according to claim 1 wherein the polyvalent cation is selected from the group consisting of Al, Cr, Ti, Zn, Mg, Zr, Fe, Ce and Sn.

11. The combination effect pigment according to claim 10, wherein the polyvalent cation is selected from the group consisting of Al(III), Zn(II), Mg(II), Ti(IV), Zr(IV), Fe(II), Fe(III), Ce(III) and Sn(IV).

12. The combination effect pigment according to claim 11, wherein the polyvalent cation has a suitable anionic counterion selected from the group consisting of chloride, nitrate and sulfate.

13. The combination effect pigment according to claim 1, wherein the carbon black loading on the effect pigment ranges from about 0.01 to about 3 wt. % based on the total weight of the uncoated substrate.

14. The combination effect pigment according to claim 9, wherein the polyvalent cation ranges from about 0.01 to about 1 wt. % based on the total weight of the uncoated substrate.

15. A paint, ink-jet, coatings, printing ink, plastic, cosmetic, glazes for ceramics and glass containing the combination effect pigment according to claim 1.

16. A cosmetic containing the combination effect pigment according to claim 1.

17. The cosmetic according to claim 16, wherein the cosmetic is in the form of sticks, ointments, creams, emulsions, suspensions, dispersions, powders or solutions.

18. The cosmetic according to claim 16, wherein the cosmetic is a lipstick, mascara preparation, blusher, eyeshadows, foundation, eyeliners, powder or nail varnishes.

19. A method of preparing the combination effect pigment according to claim 1 comprising
providing a slurry or suspension of carbon black, platelets and a polyvalent cation,
forming a hydrous oxide or hydroxide precipitate with the polyvalent cation and carbon black at a given pH,
forming at least one optical layer over the precipitate, and
drying the formed combination effect pigment, with the proviso that the at least one optical layer is different than the carbon black.

20. A method of reducing carbon black staining in an effect pigment according to claim 1 comprising the steps of:
forming a hydrous oxide or a hydroxide precipitate of carbon black and a polyvalent cation on a platelet substrate and
at least partially covering of said precipitate with at least one subsequent layer,
with the proviso that the at least one subsequent layer is different than the precipitate of carbon black and the polyvalent cation.

21. The combination effect pigment according to claim 1 comprising a layer structure that is
Substrate/$SiO_2$/Carbon Black Precipitate/$SiO_2$;
Substrate/Carbon Black Precipitate/$SiO_2$;
Substrate/Carbon Black Precipitate/$TiO_2$;
Substrate/$TiO_2$/Carbon Black Precipitate/$TiO_2$;
Substrate/Carbon Black Precipitate/$TiO_2$/$SiO_2$;
Substrate/$TiO_2$/Carbon Black Precipitate/$SiO_2$;
Substrate/$SiO_2$/$TiO_2$/Carbon Black Precipitate/$Fe_2O_3$;
Substrate/$TiO_2$/Carbon Black/$SiO_2$/Carbon Black Precipitate/$TiO_2$;
Substrate/$Fe_2O_3$/$SiO_2$/Carbon Black Precipitate/$TiO_2$/$SiO_2$;
Substrate/$SnO_2$/$TiO_2$/Carbon Black Precipitate/$TiO_2$;
Substrate/$TiO_2$/$SiO_2$/Carbon Black Precipitate/$Fe_2O_3$;
Substrate/$TiO_2$/$SiO_2$/Carbon Black Precipitate/$TiO_2$;
Substrate/$TiO_2$/Carbon Black Precipitate/$SiO_2$/$Fe_2O_3$;
Substrate/$TiO_2$/Carbon Black Precipitate/$SiO_2$/$TiO_2$;
Substrate/$Fe_2O_3$/$SiO_2$/Carbon Black Precipitate/$Fe_2O_3$;
Substrate/$Fe_2O_3$/$SiO_2$/Carbon Black Precipitate/$TiO_2$;
Substrate/$Fe_2O_3$/Carbon Black Precipitate/$SiO_2$/$Fe_2O_3$;
Substrate/$Fe_2O_3$/Carbon Black Precipitate/$SiO_2$/$TiO_2$; or
Substrate/$TiO_2$/$SiO_2$/Carbon Black Precipitate/$Cr_2O_3$.

22. The combination effect pigment according to claim 1, wherein the weight ratio of hydrous oxide or a hydroxide precipitate of carbon black to the polyvalent cation is from about 2 to 1 to about 1 to 2.

23. The combination effect pigment according to claim 1, wherein the weight ratio of hydrous oxide or a hydroxide precipitate of carbon black to the polyvalent cation is from about 1 to 1.5 to about 1.5 to 1.

* * * * *